US006779491B1

(12) United States Patent
Cho

(10) Patent No.: US 6,779,491 B1
(45) Date of Patent: Aug. 24, 2004

(54) OIL BUBBLE HEAT CONVECTION CONTROLLABLE BOTTLE DEVICE

(76) Inventor: Wen-Cheng Cho, 235 Chung-Ho Box 8-24, Taipei (TW)

( * ) Notice: Subject to any disclaimer, the term of this patent is extended or adjusted under 35 U.S.C. 154(b) by 0 days.

(21) Appl. No.: 10/418,003

(22) Filed: Apr. 15, 2003

(51) Int. Cl.[7] .................................................. A61F 7/08

(52) U.S. Cl. ...................................... 122/4 R; 392/443

(58) Field of Search .......................... 122/4 R; 392/341, 392/344, 443, 444, 445, 448

(56) References Cited

U.S. PATENT DOCUMENTS 3,804,076 A * 4/1974 Fant et al. .................. 126/261
3,892,945 A * 7/1975 Lerner ........................ 219/437
4,716,278 A * 12/1987 Cappe et al. ............... 219/521
6,234,165 B1 * 5/2001 Creighton et al. ..... 126/263.06

* cited by examiner

*Primary Examiner*—Gregory Wilson

(57) ABSTRACT

An oil bubble heat convection controllable bottle device comprises a bottle having a hollow inner space. Sterile liquid and decorations are disposed in the inner space. A bottom of the bottle is installed with a heating seat. A heating source is installed within the heating seat. A bottom seat is installed at a bottom of the bottle and a top of the heat source. A plurality of through holes are formed on the bottom seat. Thus, the bottom of the bottle is heated uniformly. The bottom seat is made of heat-tolerable silicone. The through holes have different sizes. The bottom seat installed at the bottom of the bottle is stuck to a lower side of the bottle by heat-tolerable glue.

7 Claims, 9 Drawing Sheets

OIL BUBBLE HEAT CONVECTION CONTROLLABLE BOTTLE DEVICE

FIELD OF THE INVENTION

The present invention relates to decorative bottles, and particularly to an oil bubble heat convection controllable bottle device, wherein the bottom seat is placed below the bottom of a bottle, and a plurality of through holes are formed on the bottom seat so that the bottom of the bottle is not heated uniformly and thus the oil bubbles within the bottle can flow with special paths due to non-uniform heat conventions within the bottle.

BACKGROUND OF THE INVENTION

In the prior art glass bottle, a hollow bottle is filled with sterile liquid and decorations. The bottom of the bottle has a heating seat. A heat source is disposed in the heating seat. The liquid in the bottle is heated by radiation and heat convection and thus the decorations flow with the convection of liquid.

Above mentioned glass bottle, as shown in FIG. 1, a two layer heat convection glass bottle has a bottle body 2 and an air-tight bottom seal cover 21. An inner bottle 7 is placed within the bottle body 2. A bottle body 2 of the inner bottle 7 is fixed to the bottom seal cover 21. Sterile liquid A and decorations B are placed between the bottle body 2 and the inner bottle 7. Sterile liquid A1 and decorations B1 are placed in the inner bottle 7. Furthermore, the inner bottle 7 has a seal plug 71 and the bottle body 2 has a seal plug 23. Moreover, the inner bottle 7 can be placed in a container 72, and the bottle body 2 is fixed on the seal cover 21 by using fixing units 222. The space between the inner bottle 7 and the bottle body 2 can not communicate to each other. The bottom seal cover 21 is made of rigid material, such as glass, instead of conventional used rubber plug so that the bottom seal cover 21 will not deform due to heat. The glass bottom seal cover 21 will not deform due to heat and heat at the lower side can be transferred to the space between the inner bottle 7 and the bottle body 2.

The liquids A and A1 may be the same or different colors, specifications and shapes. To have a preferred decorating effect, the liquids A and B have different colors and specifications. The decorations B are gold-like pieces and the liquid A1 is liquid wax. The decorations B and B1 have different colors and shapes. The bottle body 2 is placed upon an opening of the heating seat 1. A heat source is placed in the heating seat. The heat source is near the bottom seal cover 21, but not in contact with the bottom seal cover 21. The heat source heats the bottom seal cover 21 through radiation and convection. The sterile liquid in the bottle body 2 and inner bottle is unstable with a hot upper portion and a cold lower portion. Thereby, heat convection occurs. Thereby, a special decorating effect is presented. The heat source may be a candle, that is, a suspending frame is installed to the heating seat 1. A temperature-tolerable glass plate 5 is clamped on the heating seat 1 by using a clamping unit 6. A candle 3 is placed at a bottom of the suspending frame 4.

Other than gold-like pieces (made of heat-tolerable PVC), the decorations B and B1 may be made as snow-like pieces, or small light malls so as to present different visual effect.

In above mentioned prior art, since the heat is uniformly heated to the bottom of the bottle, the scenery is dull and not vivid.

SUMMARY OF THE INVENTION

Accordingly, the primary object of the present invention is to provide an oil bubble heat convection controllable bottle device, wherein an oil bubble heat convection controllable bottle device which comprises a bottle having a hollow inner space. Sterile liquid and decorations are disposed in the inner space. A bottom of the bottle is installed with a heating seat. A. heating source is installed within the heating seat. A bottom seat is installed at a bottom of the bottle and a top of the heat source. A plurality of through holes are formed on the bottom seat; thus, the bottom of the bottle is heated uniformly. The bottom seat is made of heat-tolerable silicone. The through holes have different sizes. The bottom seat installed at the bottom of the bottle is stuck to a lower side of the bottle by heat-tolerable glue.

The various objects and advantages of the present invention will be more readily understood from the following detailed description when read in conjunction with the appended drawing.

BRIEF DESCRIPTION OF THE PREFERRED EMBODIMENTS

Figure 1:
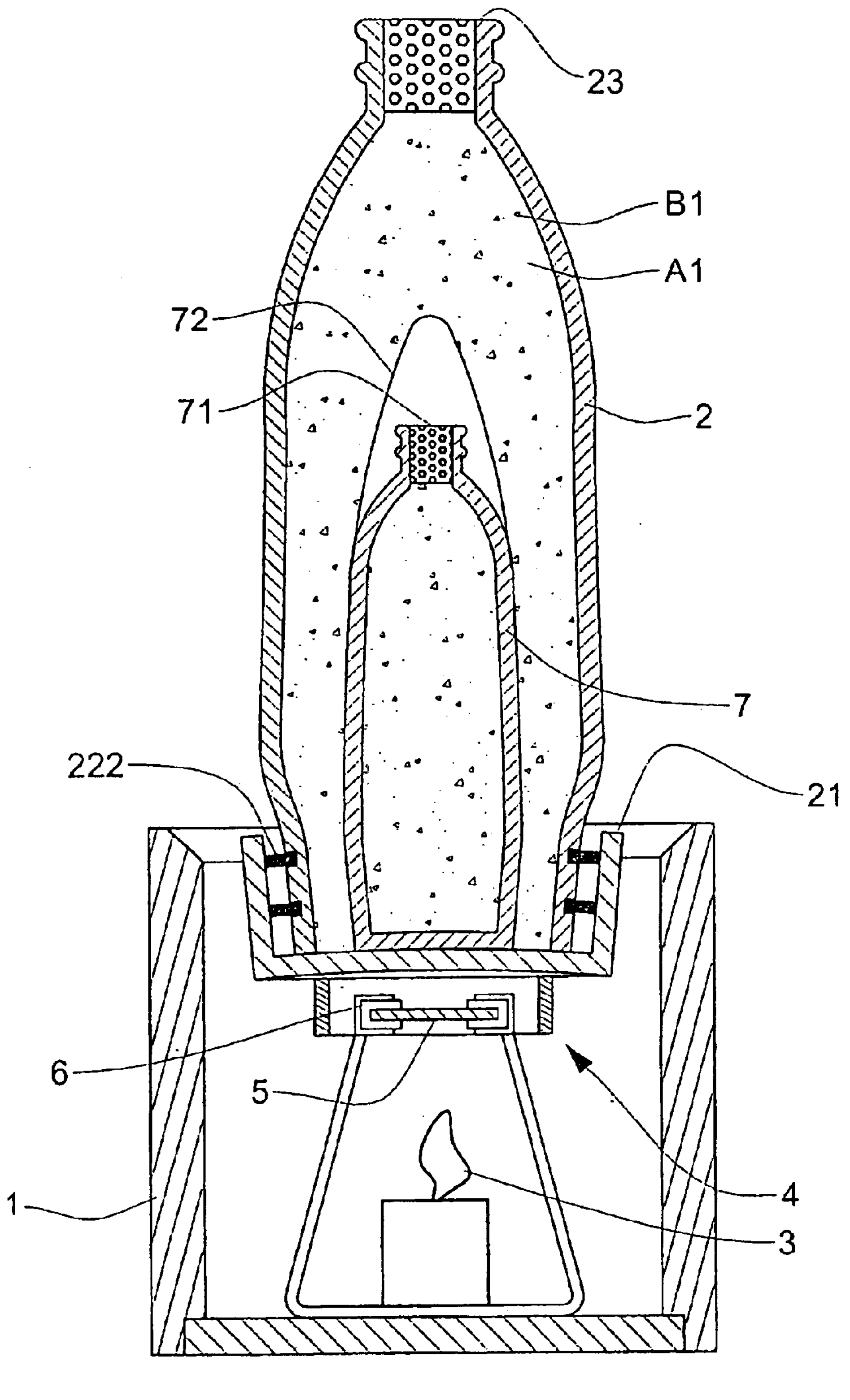
Fig. 1 (PRIOR ART)
FIG. 1 is a cross section view showing the prior art glass bottle.
Figure 2:
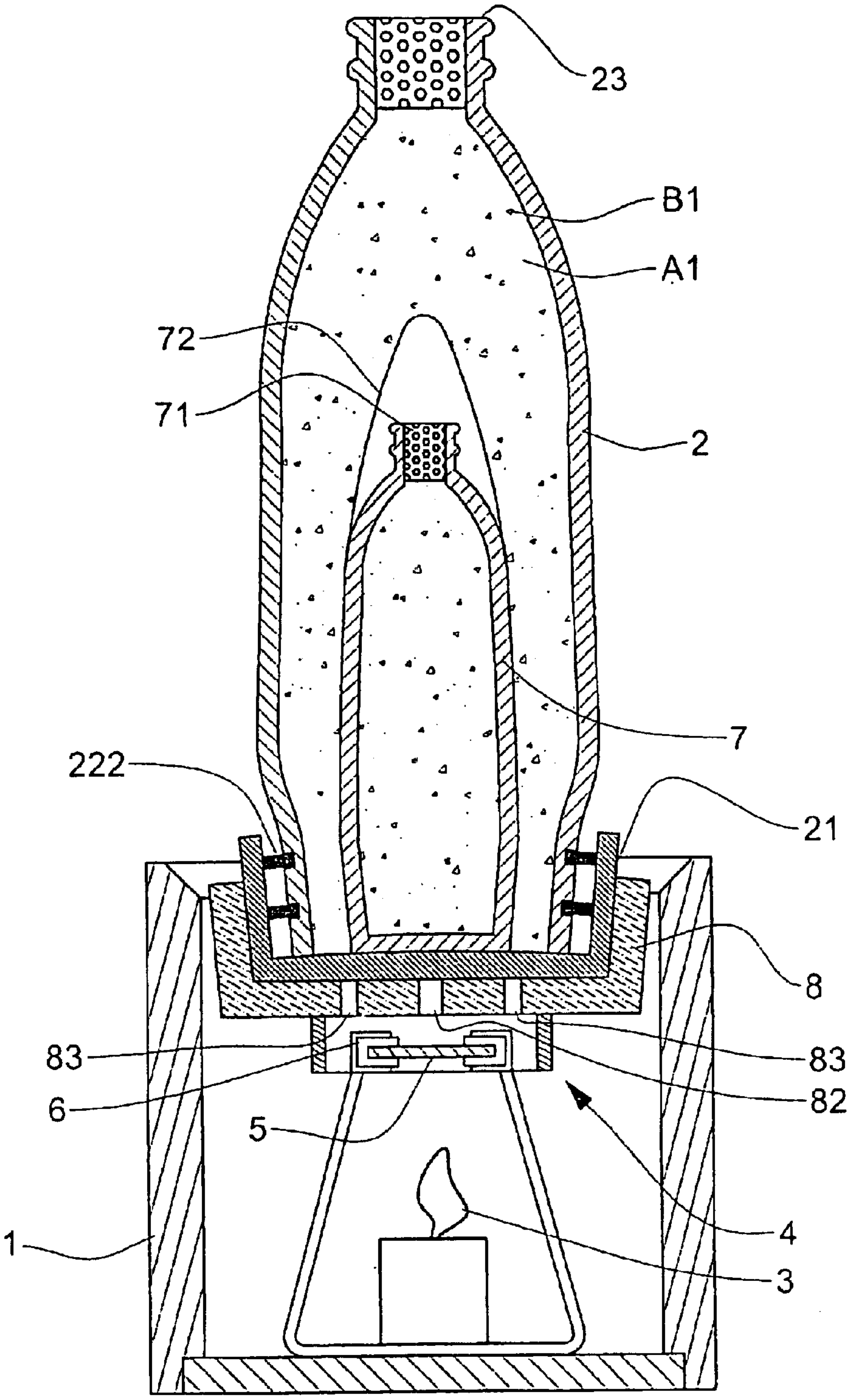
FIG. 2 is a cross section view of the bottle of the present invention.
Figure 3:
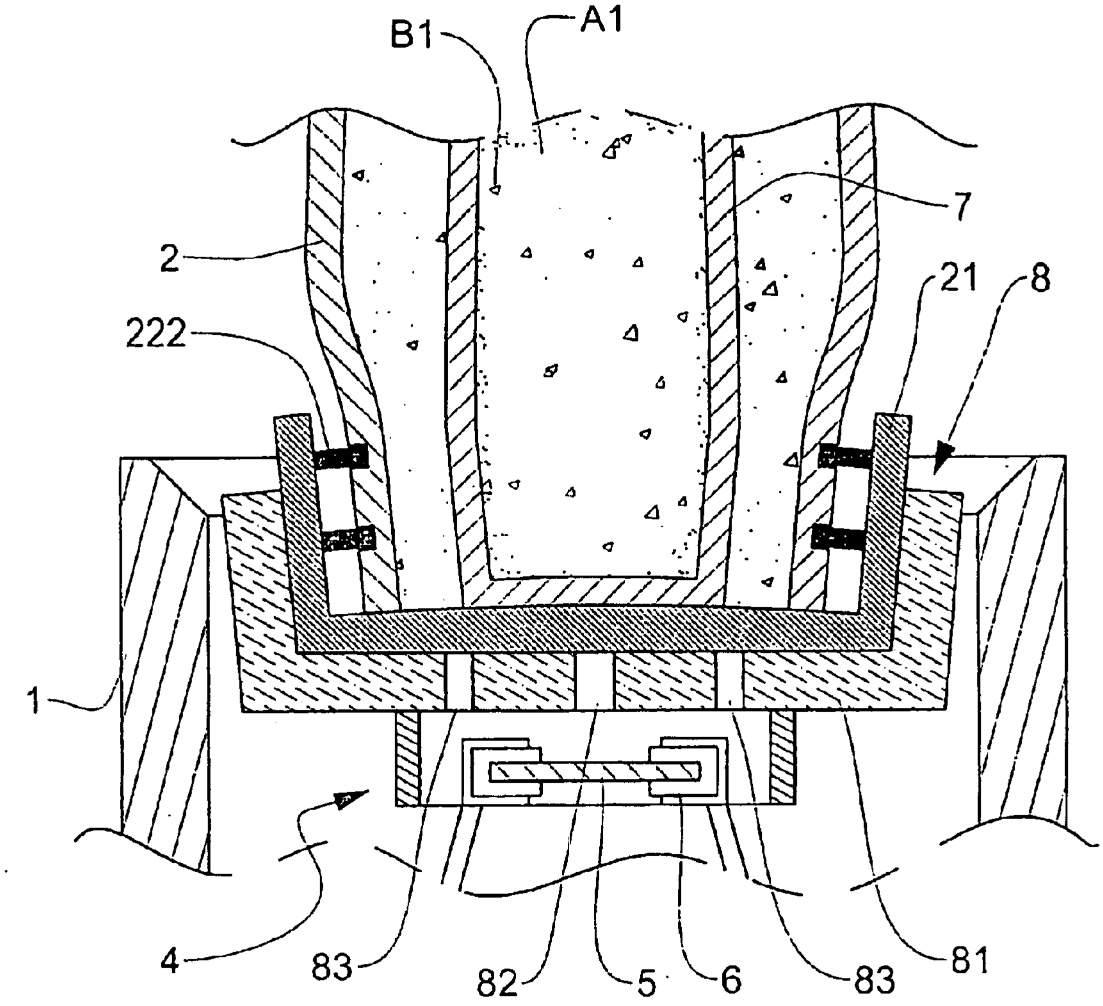
FIG. 3 is a partial enlarged view of the bottle of the present invention.
Figure 5:
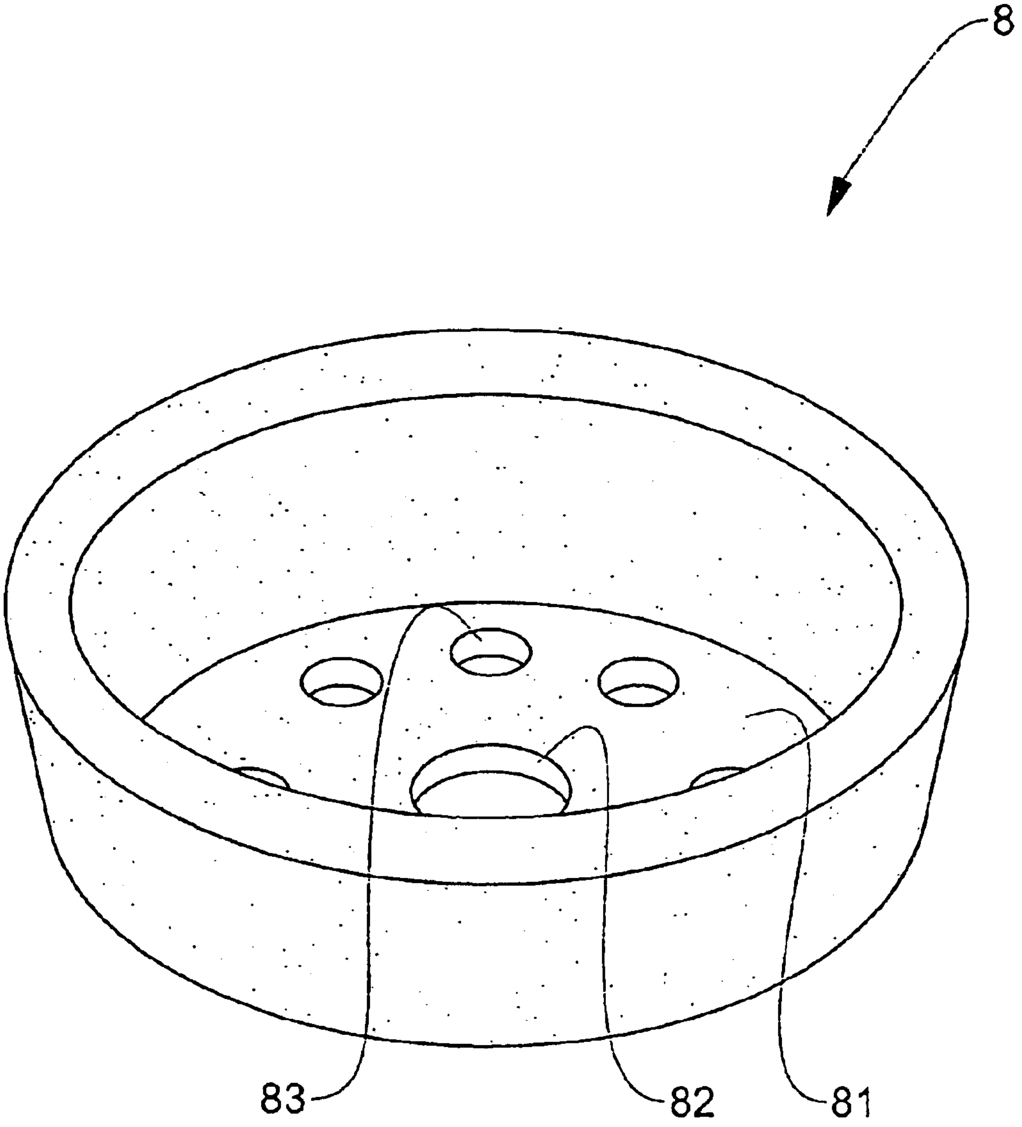
FIG. 5 is a perspective view about the bottom seat of the present invention.

Referring to FIGS. 2 and 3, the oil bubble heat convection controllable bottle seat of the present invention is illustrated. In the present invention, a bottom of the bottom seal cover 21 is installed with a bottom seat 8. It should be noted in FIGS. 2 and 3, the elements having same numerals as those in FIG. 1 represent the same elements of FIG. 1, and thus the details will not be further described here. The bottom seat 8 overlaps with the bottom sealing cover 21. The bottom seat 8 is made of heat-tolerable silicone, but the present invention is not confined to this material. A bottom surface 81 of the bottom seat 8 is formed with a plurality of through holes 82, 83 which can be positioned anywhere and with any desired sizes, as shown in FIG. 5. The bottom sealing cover 21 is stuck to the bottom seat 8 by heat-tolerable glue.

Figure 4:
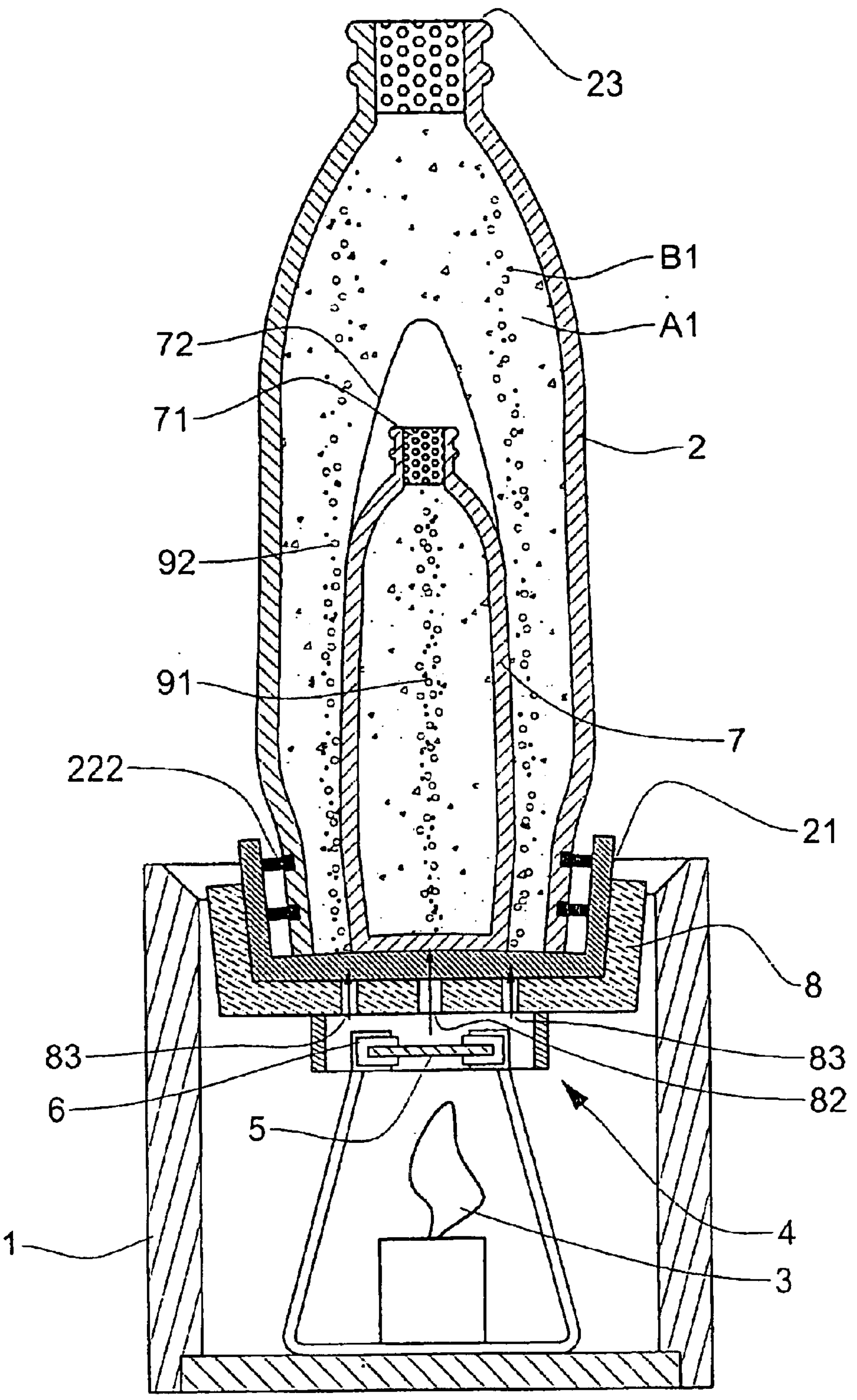
FIG. 4 shows the operation of the bottle of the present invention.

The bottom seat 8 is placed at an upper portion of a heating seat 1 with a candle 3 placed therein. When the candle 3 generates heat, the heat from the candle 3 is transferred to the bottom seal cover 21. Then, part of heat is transferred rapidly through the through holes 82, 83. Thereby, the portions of the bottom seal cover 21 corresponding to the through holes 82, 83 are heated so as to have a higher temperature than those portions not being heated. The heat will cause the oil bubbles 91, and 92 in the bottles to flow through heat convection, as shown in FIG. 4. This is different from the prior art.

It is obviously, in the prior art, the whole bottom of the bottle is heated uniformly so that the heat convection occurs everywhere in the bottle. On the contrary, in the present invention, since through holes are formed, the bottom is not uniformly heated. Thereby, the flow of the oil bubbles are special.

Figure 6:
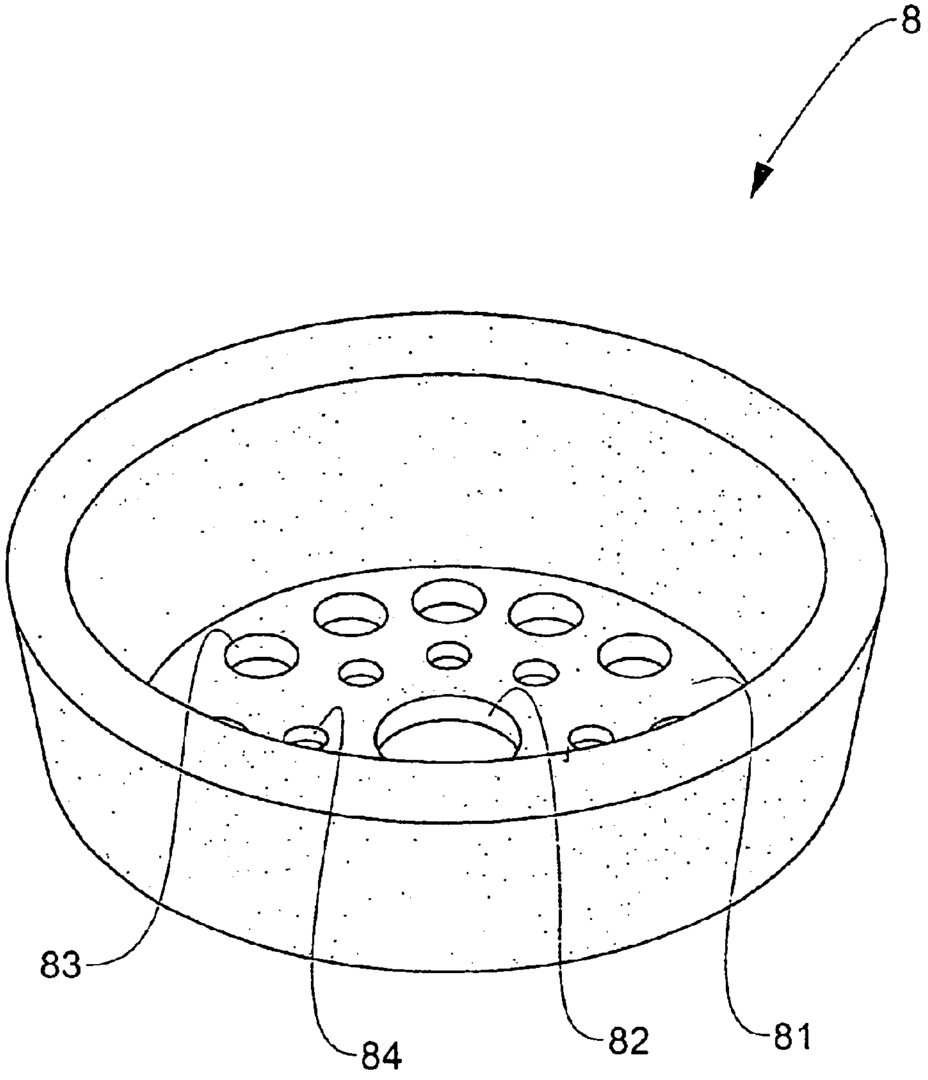
FIG. 6 is a perspective view of another embodiment about the bottom seat of the present invention.

The positions, numbers and diameters of the through holes of the bottom seat 8 are changed as desired. With reference to FIG. 6, another embodiment of the present invention is illustrated. A center of the bottom surface 81 has a larger through hole 82. An outer periphery of the larger through hole 82 has a plurality of smaller through holes 84 arranged around the larger through hole 82 and a plurality of middle through holes 83 are arranged around the smaller through holes 84. Therefore the sizes and positions of the oil bubbles are controllable as desired.

Figure 7:
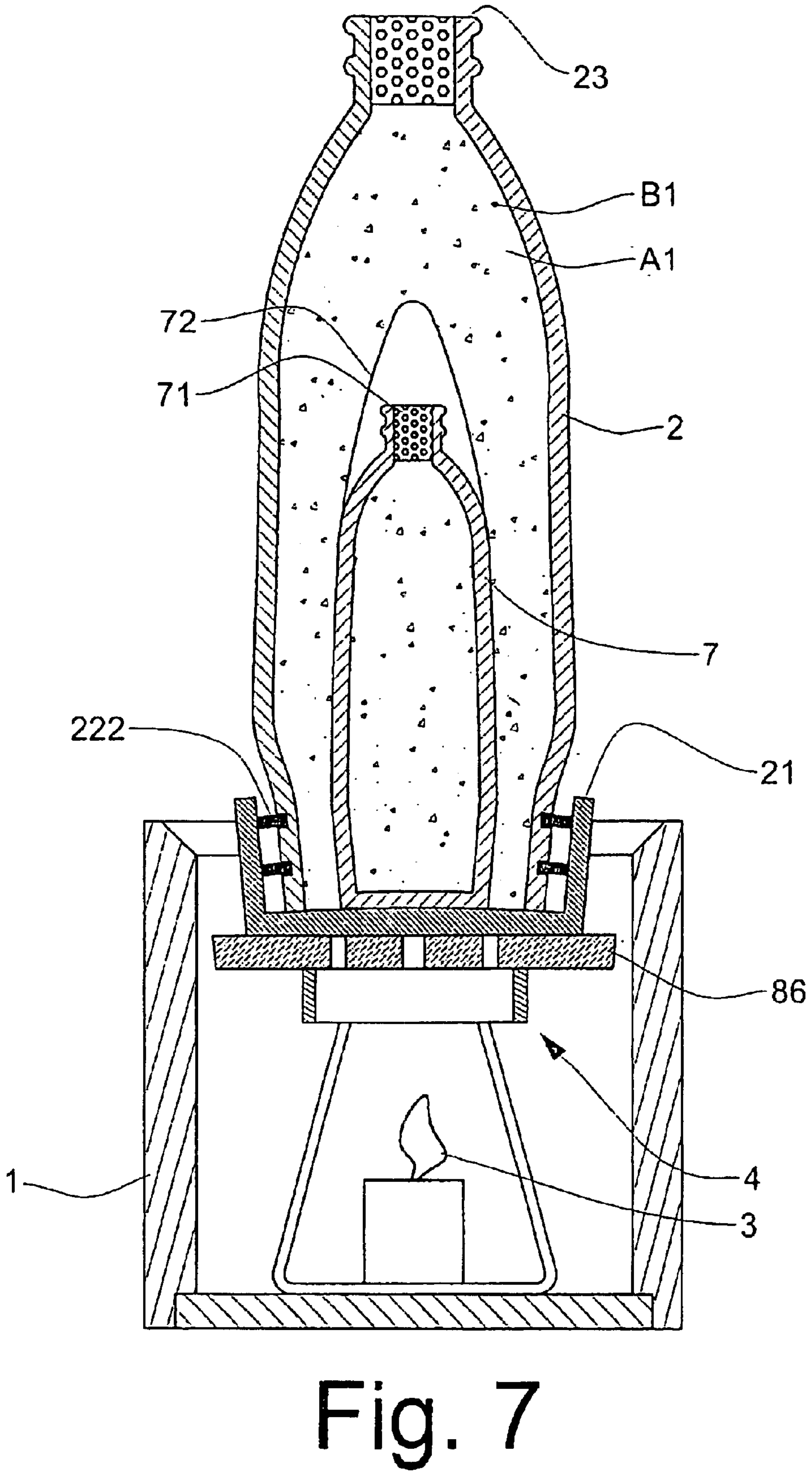
FIG. 7 shows one structure of the present invention, where the heat-tolerable glass plate is not used.
Figure 8:
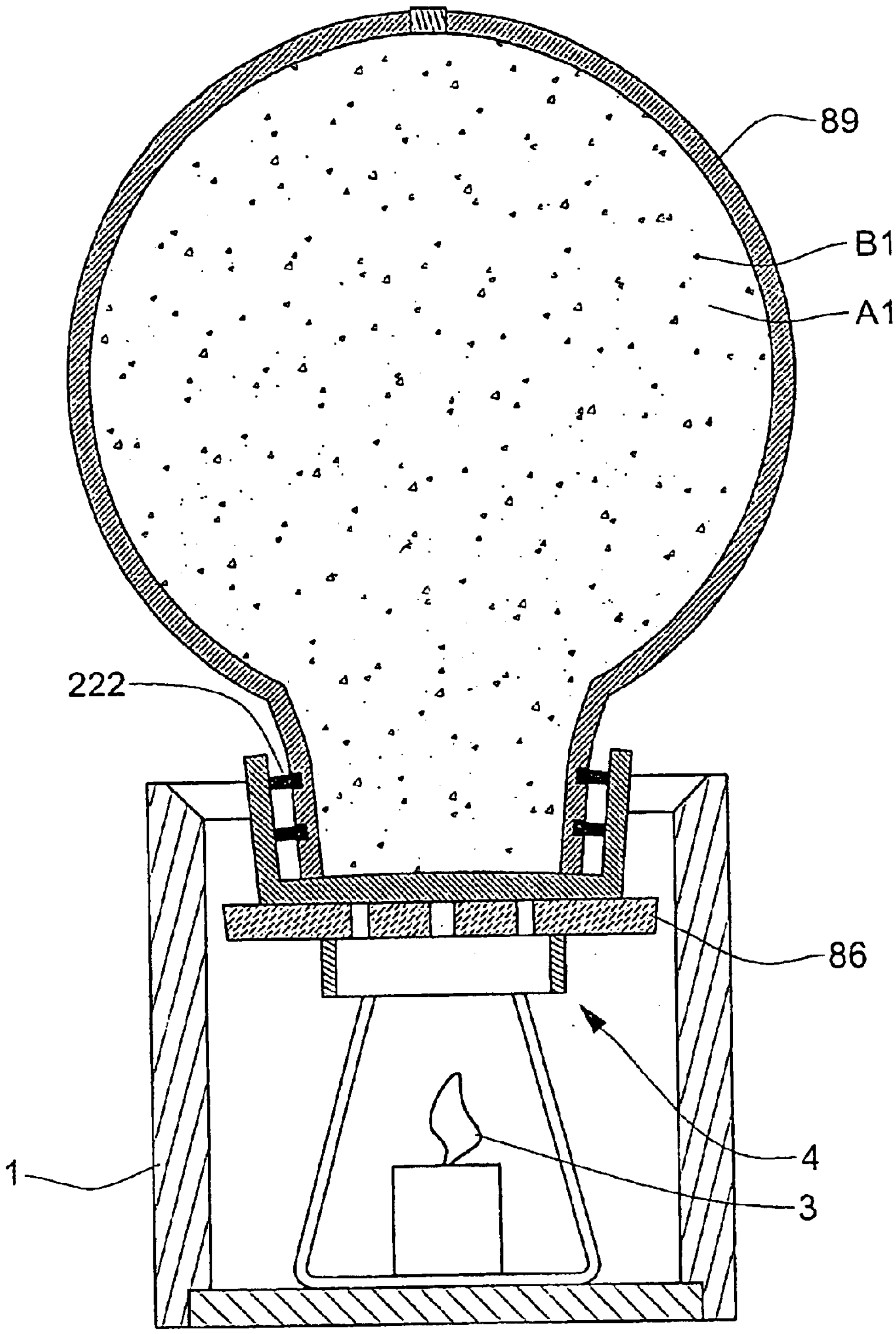
FIG. 8 shows another embodiment of the present invention, where the bottle is a single layer ball.
Figure 9:
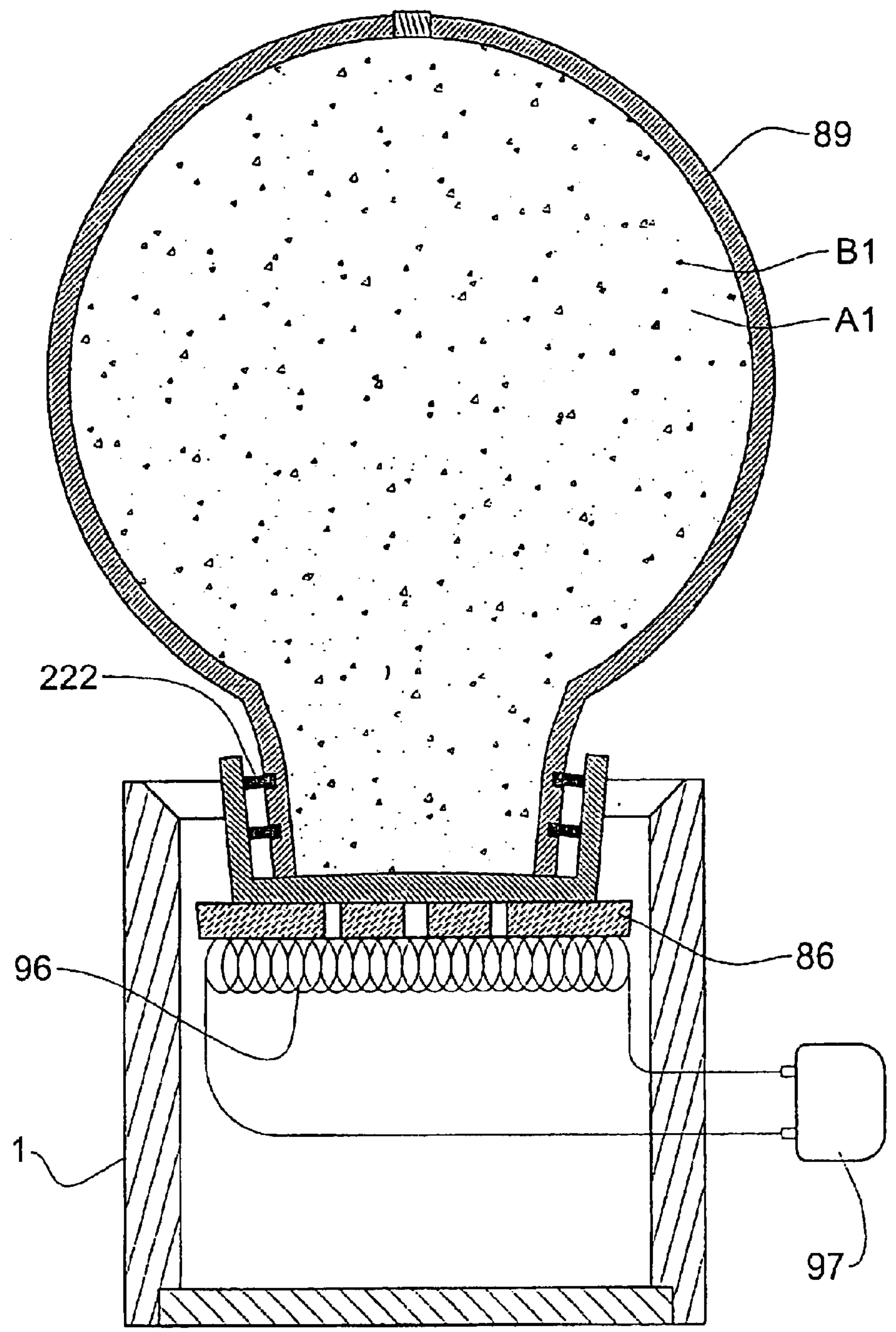
FIG. 9 shows another embodiment of the present invention, where electric heating silk is used as a heat source.

In the present invention, the temperature-tolerable glass plate 5 used in the prior art can be cancelled, as shown in FIGS. 7 and 8. With reference to FIG. 8, another embodiment of the present invention is illustrated. The bottle is made as a single layer ball 89. The bottom seat 8 is a flat seat 86 as shown in FIGS. 8 and 9.

The heat source below the bottom seat 8 can be an annular electric heating silk 96 other than the candle 3. With reference to FIG. 9, the electric heating silk 96 can be adhered to be below the bottom seat 8 and is connected to a temperature adjuster 97 for controlling temperature.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An oil bubble heat convection controllable bottle device comprising a bottle having a hollow inner space; sterile liquid and decorations being disposed in the inner space; a bottom of the bottle being installed with a heating seat; a heating source being installed within the heating seat;

a heat seat installed below the bottom of the bottle a seal cover for covering an upper portion of the heat seat;

a bottom seat installed below and on a bottom of the seal cover; a bottom surface of the bottom seat being formed with a plurality of through holes; the bottom seat being placed above the heating seat;

a heat source installed on a bottom of the beat seat and below the bottom seat; heat generated by the heat source being transferred to the bottom seat; part of heat being transferred rapidly through the through holes; thereby, the portions of the bottom seal cover corresponding to the through holes being heated so as to have a higher temperature than those portions not being heated; and the heat will cause the oil bubbles in the bottles to flow through heat convection.

2. The oil bubble heat convection controllable bottle device as claimed in 1, wherein a temperature tolerance glass plate is located above the heat source and below the bottom seat.

3. The oil bubble heat convection controllable bottle device as claimed in 1, wherein a center of the bottom surface has a larger through hole; an outer periphery of the larger through hole has a plurality of smaller through holes arranged around the larger through hole and a plurality of middle through holes are arranged around the smaller through holes; therefore the sizes and positions of the oil bubbles are controllable.

4. The oil bubble heat convection controllable bottle device as claimed in 1, wherein the bottle is made as a single layer ball; the bottom seat is a flat seat.

5. The oil bubble heat convection controllable bottle device as claimed in 1, wherein the heat source is a candle.

6. The oil bubble heat convection controllable bottle device as claimed in 1, wherein the heat source is an annular electric heating silk.

7. The oil bubble heat convection controllable bottle device as claimed in 1, wherein the bottom seat is made of heat-tolerable silicon.

* * * * *